US012678285B2

(12) United States Patent (10) Patent No.: US 12,678,285 B2
Ozaki (45) Date of Patent: Jul. 14, 2026

(54) VALVE CUSP SIZER

(71) Applicant: Shigeyuki Ozaki, Tokyo (JP)

(72) Inventor: Shigeyuki Ozaki, Tokyo (JP)

( * ) Notice: Subject to any disclaimer, the term of this patent is extended or adjusted under 35 U.S.C. 154(b) by 711 days.

(21) Appl. No.: 17/287,599

(22) PCT Filed: Oct. 11, 2019

(86) PCT No.: PCT/JP2019/040159
§ 371 (c)(1),
(2) Date: Apr. 22, 2021

(87) PCT Pub. No.: WO2020/085112
PCT Pub. Date: Apr. 30, 2020

(65) Prior Publication Data
US 2021/0386548 A1 Dec. 16, 2021

(30) Foreign Application Priority Data

Oct. 25, 2018 (JP) ................................. 2018-200784

(51) Int. Cl.
*A61F 2/24* (2006.01)
*A61F 2/76* (2006.01)
(52) U.S. Cl.
CPC .............. *A61F 2/2496* (2013.01); *A61F 2/76* (2013.01); *A61F 2002/762* (2013.01)
(58) Field of Classification Search
CPC .... A61F 2/2496; A61F 2/76; A61F 2002/762; A61B 5/1076; A61B 5/103; G09B 23/30
See application file for complete search history.

(56) References Cited

U.S. PATENT DOCUMENTS 5,972,030 A * 10/1999 Garrison .......... A61B 17/06061
623/2.11
2010/0249661 A1 9/2010 Righini et al.
2015/0005671 A1* 1/2015 Gollinger .............. A61F 2/2496
600/587
2015/0265403 A1* 9/2015 Keranen ............... A61F 2/2427
264/153

FOREIGN PATENT DOCUMENTS

CN 206453856 U 9/2017
EP 3 192 472 A1 7/2017
JP 2009-077838 A 4/2009

OTHER PUBLICATIONS

Extended European Search Report issued Oct. 15, 2021 in European Application No. 19876068.8.
International Search Report for PCT/JP2019/040159, dated Dec. 24, 2019.
Chinese Office Action issued Jan. 12, 2024 in Application No. 201980069138.8.

(Continued)

*Primary Examiner* — Devin B Henson
(74) *Attorney, Agent, or Firm* — Sughrue Mion, PLLC

(57) ABSTRACT

A valve cusp sizer includes a back surface brought into contact with a living body, and a hole that is formed on the top surface at a distance from the center in a left-right direction toward one side in the left-right direction and into which a support rod is inserted.

20 Claims, 6 Drawing Sheets

(56)     References Cited

OTHER PUBLICATIONS

Communication dated Nov. 12, 2024 issued by the State Intellectual Property Office of the P.R.China in application No. 201980069138. 8.

Communication dated Jun. 8, 2024 issued by the State Intellectual Property Office of the P.R.China in application No. 201980069138. 8.

European Office Action dated Feb. 23, 2026, issued in European application No. 19876068.8.

* cited by examiner

VALVE CUSP SIZER

CROSS REFERENCE TO RELATED APPLICATIONS

This application is a National Stage of International Application No. PCT/JP2019/040159 filed Oct. 11, 2019, claiming priority based on Japanese Patent Application No. 2018-200784 filed Oct. 25, 2018, the entire contents of each of which are herein incorporated by reference in their entireties.

TECHNICAL FIELD

The present invention relates to a valve cusp sizer.

BACKGROUND ART

An invention for measuring the size of an aortic valve cusp is disclosed, for example, in Patent Document 1 as a valve cusp sizer. The valve cusp sizer has an arcuate surface, and stylus parts that come into contact with a commissure part of the valve cusp and is provided at both ends of the arcuate surface. The valve cusp sizers are provided in multiple sizes with arcuate surfaces having different lengths, and each of the plurality of valve cusp sizers has a handle that is gripped by an operator. When measuring the size of a valve cusp, an operator inserts the valve cusp sizer into a valve ring part of the aorta and confirms the nominal diameter of the valve cusp sizer where the positions of the two stylus parts coincide with the position of the commissure part.

CITATION LIST

Patent Document

Patent Document 1: Japanese Patent Application Laid-Open No. 2009-77838

SUMMARY OF THE INVENTION

Problems to be Solved by the Invention

In the valve cusp sizer disclosed in Patent Document 1, a handle is attached to the center of a partial cylinder that forms an arcuate surface. When measuring the size of the valve cusp, the valve cusp sizer is pressed against the inner wall of the aorta, but in a case that a handle is attached to the center of the partial cylinder that forms the arcuate surface, the valve cusp sizer may be pushed in the radial direction of the aorta. In this case, the aorta spreads and the size of the valve cusp cannot be measured accurately.

An object of the present invention is to provide a valve cusp sizer capable of accurately measuring the size of a valve cusp.

Means for Solving the Problems

The present invention provides a valve cusp sizer including: a back surface brought into contact with a living body; and a hole that is formed on the top surface at a predetermined distance from the center in a left-right direction to (at least) one side in the left-right direction and into which a support rod is to be inserted.

In the present invention, the valve cusp sizer may have a portion to be supported that protrudes from the front in the opposite direction to the back at left and right end portions, and the hole may be formed on the top surface of the portion to be supported.

Moreover, in the present invention, the valve cusp sizer may further include a hole into which the support rod is inserted at a predetermined distance from the center in the left-right direction in a direction opposite to the one side.

Furthermore, in the present invention, the hole may be inclined relative to the bottom surface.

Advantageous Effect of the Invention

The present invention enables the size of a valve cusp to be accurately measured.

MODE FOR CARRYING OUT THE INVENTION

Figure 1:
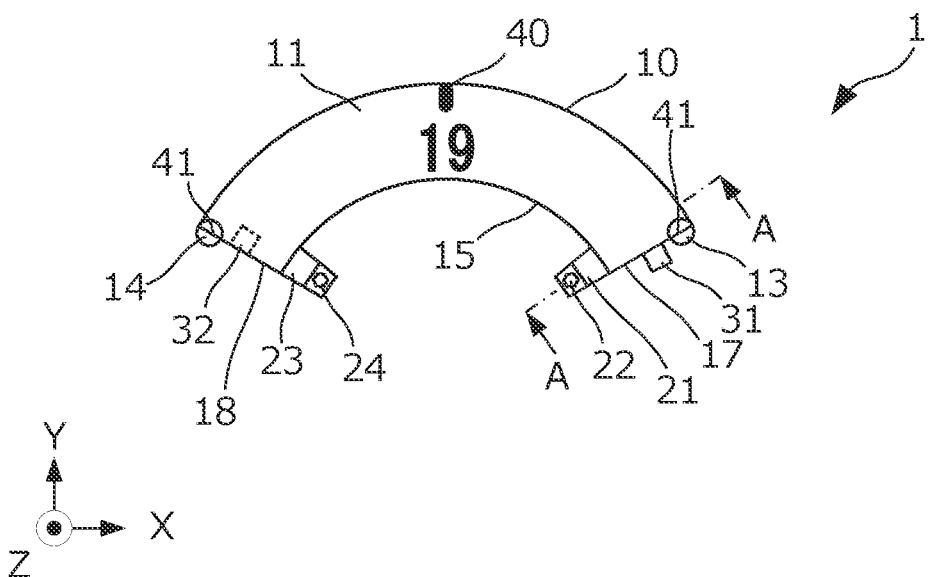
FIG. 1 is a top view of a valve cusp sizer 1 according to an embodiment of the present invention.
Figure 2:
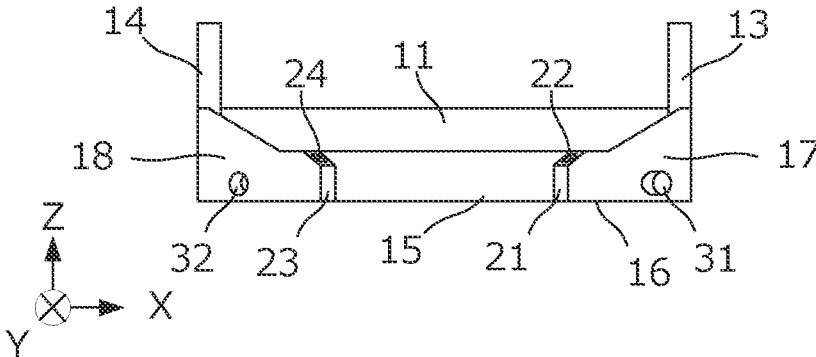
FIG. 2 is a front view of the valve cusp sizer 1.
Figure 3:
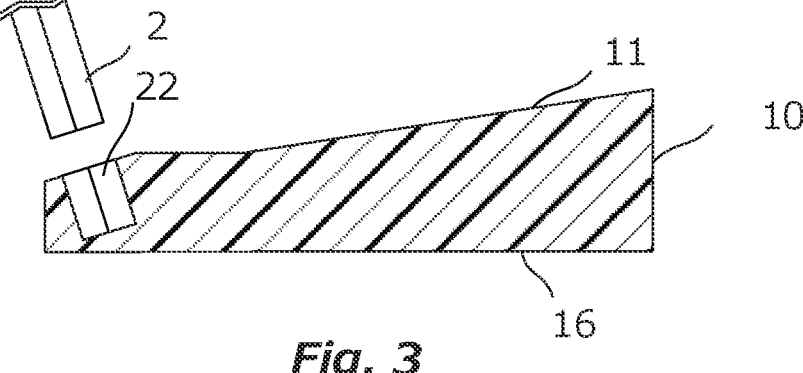
FIG. 3 is an A-A line cross section of FIG. 1.

FIG. 1 is a top view of a valve cusp sizer 1 according to an embodiment of the present invention, and FIG. 2 is a front view of the valve cusp sizer 1. In addition, FIG. 3 is an A-A line cross section of FIG. 1. The valve cusp sizer 1 is a surgical instrument used in an aortic valvuloplasty or the like.

The basic shape of the valve cusp sizer 1 is a hollow cylinder divided into three equal parts in the direction of the [relative to the] central axis. In other words, the valve cusp sizer 1 has an angle of 120 degrees between a line made by extending one end face 17 in the circumferential direction (left-right direction) and a line made by extending the other end face 18 in the circumferential direction. The valve cusp sizer 1 is made of synthetic resin. The material of the valve cusp sizer 1 is not limited to synthetic resin, and may be any other appropriate material.

The valve cusp sizer 1 has an outer peripheral surface 10 (back surface) that is brought into contact with the vascular inner wall of a patient's aorta. The outer peripheral surface 10 has an arcuate shape when the valve cusp sizer 1 is viewed from above. Further toward the center than the outer peripheral surface 10, there is formed a top surface 11 that spreads from the outer peripheral surface 10 to an inner peripheral surface 15 (front). Comparing the height of the outer peripheral surface 10 with the height of the inner peripheral surface 15, the outer peripheral surface 10 is higher than the inner peripheral surface 15, and the top surface 11 is inclined with respect to the bottom surface 16. The radial cross section of the top surface 11 may be either straight or curved.

The valve cusp sizer 1 has multiple sizes, and the outer peripheral surface 10 of each has a different circumferential length. For the size of the valve cusp sizer 1, for example, the diameter of the cylindrical shape before being divided into three equal parts is used as the nominal diameter for identifying the size of the valve cusp. The nominal diameter is an odd-number from 17 to 35. The nominal diameter of the valve cusp sizer 1 is printed on the top surface 11, and is indicated as 19 in the case of the valve cusp sizer 1 illustrated in FIG. 1. The nominal diameter may be an even number, or may consist of both an odd number and an even number. In addition, the size of the nominal diameter may be less than 17 or more than 35.

A cylindrical first stylus part 13 is formed at one end of the top surface 11 in the circumferential direction, and a cylindrical second stylus part 14 is formed at the other end of the top surface 11 in the circumferential direction. Marks 41 are provided at the upper end of the first stylus part 13 and at the upper end of the second stylus part 14 for alignment with the commissure part. The angle between a line connecting the center and the mark 41 on the first stylus part 13 and a line connecting the center and the mark 41 on the second stylus part 14 is 120 degrees. The first stylus part 13 and the second stylus part 14 come into contact with the commissure part of the valve cusp when the size of the valve cusp is measured. The height from the bottom surface 16 to the upper end of the first stylus part 13 is the same as the height from the bottom surface 16 to the upper end of the second stylus part 14, and the height is greater than the height from the bottom surface 16 to the top surface 11. This [configuration] facilitates measurement of the size of the valve cusp by bringing the upper end of the first stylus part 13 and the upper end of the second stylus part 14 into contact with the commissure part.

Figure 4:
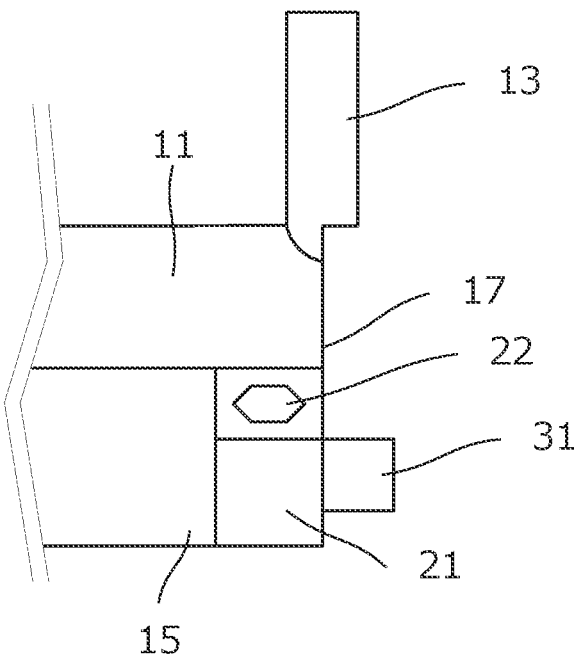
FIG. 4 is a diagram in which an end portion of the valve cusp sizer 1 is viewed in a radial direction.

FIG. 4 is a diagram in which the first stylus part 13 is viewed radially from the center of the valve cusp sizer 1. In a case that the first stylus part 13 has a cylindrical shape, preferably a half of the cylindrical shape protrudes from the circumferential end face 17 in the circumferential direction. The second stylus part 14 has the same configuration as the first stylus part 13.

In addition, a mark 40 is provided on the top surface 11. The mark 40 is provided at a position where the angle between the end face 17 and a virtual line extending from the mark 40 to the center of the valve cusp sizer 1 is 60 degrees. The mark 40 is colored differently from other parts. The mark 40 is used in drawing with a skin marker a start position of suturing of the valve cusp.

In setting a reference plane that passes through the mark 40 orthogonal to the central axis of the first stylus part 13 and the central axis of the second stylus part 14 as an intersection of the first stylus part 13, and the reference plane as an intersection $Z_R$ and an intersection of the second stylus part 14 and the reference plane as an intersection $Z_L$, preferably each of a distance L1 from the intersection $Z_R$ to the upper end of the first stylus part 13 and a distance L2 from the intersection $Z_L$ to the upper end of the second stylus part 14 is 4 mm or more. Moreover, the lower ends of both end portions in the circumferential direction of the outer peripheral surface 10 (the lower end of the outer peripheral surface 10 side of the end face 17 and the lower end of the outer peripheral surface 10 side of the end face 18) are preferably below the reference plane described above. If each of the distance L1 and the distance L2 is less than 4 mm and the lower ends of both end portions in the circumferential direction of the outer peripheral surface 10 are above the reference plane, and if the lower ends of both end portions in the circumferential direction of the outer peripheral surface 10 are above the reference plane, the outer peripheral surface 10 of the valve cusp sizer 1 tends to tilt with respect to the blood vessel wall when the valve cusp sizer 1 is brought into contact with the aorta. If the outer peripheral surface 10 of the valve cusp sizer 1 comes in contact with the blood vessel wall in a tilted position (with respect thereto), the first stylus part 13 and the second stylus part 14 also tilt and thus are measured to have a size that is different from their actual size. If each of the distance L1 and the distance L2 is 4 mm or more and the lower ends of both end portions in the circumferential direction of the outer peripheral surface 10 are above the reference plane, the outer peripheral surface 10 of the valve cusp sizer 1 is less likely to tilt with respect to the blood vessel wall and the first stylus part 13 and the second stylus part 14 also are less likely to tilt, and thus the size of the valve cusp can be accurately measured.

Further toward the center than the inner peripheral surface 15 of the valve cusp sizer 1, a portion to be supported 21 and a portion to be supported 23 are formed. The portion to be supported 21 is formed to protrude from the position of the inner peripheral surface 15 toward the center with a predetermined width from the end face 17 in the circumferential direction. A hexagonal hole 22 is formed on the top surface of the portion to be supported 21. The hole 22 is located at a predetermined distance from the center in the left-right direction toward the right. The portion to be supported 23 is formed to protrude from the position of the inner peripheral surface 15 to the center side with a predetermined width from the end face 18 in the circumferential direction. A hexagonal hole 24 is formed on the top surface of the portion to be supported 23. The hole 24 is located at a predetermined distance from the center in the left-right direction toward the left. The height of the inner peripheral surface 15 is the same as the height from the bottom surface 16 to the upper end of the portion to be supported 21 and to the upper end of the portion to be supported 23. The height from the bottom surface 16 to the upper end of the portion to be supported 21 and of the portion to be supported 23, however, may be lower or higher than the height of the inner peripheral surface 15.

The hole 22 and the hole 24 are holes into which the support rod 2 for supporting the valve cusp sizer 1 is inserted. In the portion to be supported 21, the surface on which the hole 22 is open is inclined, and the hole 22 has a predetermined angle with respect to the bottom surface 16 of the valve cusp sizer 1. In addition, the surface where the hole 24 is open in the portion to be supported 23 is inclined, and the hole 24 has a predetermined angle with respect to the bottom surface 16 of the valve cusp sizer 1.

The support rod 2 is a rod with a hexagonal cross section. When the support rod 2 is inserted into the hole 22 or the hole 24, the support rod 2 supports the valve cusp sizer 1. Since the valve cusp sizer 1 is supported by the support rod 2, the portion to be supported 21 and the portion to be supported 23 need only have a width greater than that of the support rod 2 in the circumferential direction, a height at which the support rod 2 is able to be inserted, and a radial length at which the support rod 2 is able to be inserted.

On the end face 17, a convex portion 31 is formed in the circumferential direction. The convex portion 31 has a circular cross section and protrudes from the end face 17 with a predetermined length. On the end face 18, a circular concave portion 32 is formed in the circumferential direction with a predetermined depth. The depth of the concave portion 32 is a depth at which the convex portion 31 formed in another valve cusp sizer 1 fits. The convex portion 31 and the concave portion 32 are examples of the connecting means according to the present invention.

Figures 5A, 5B, 5C:
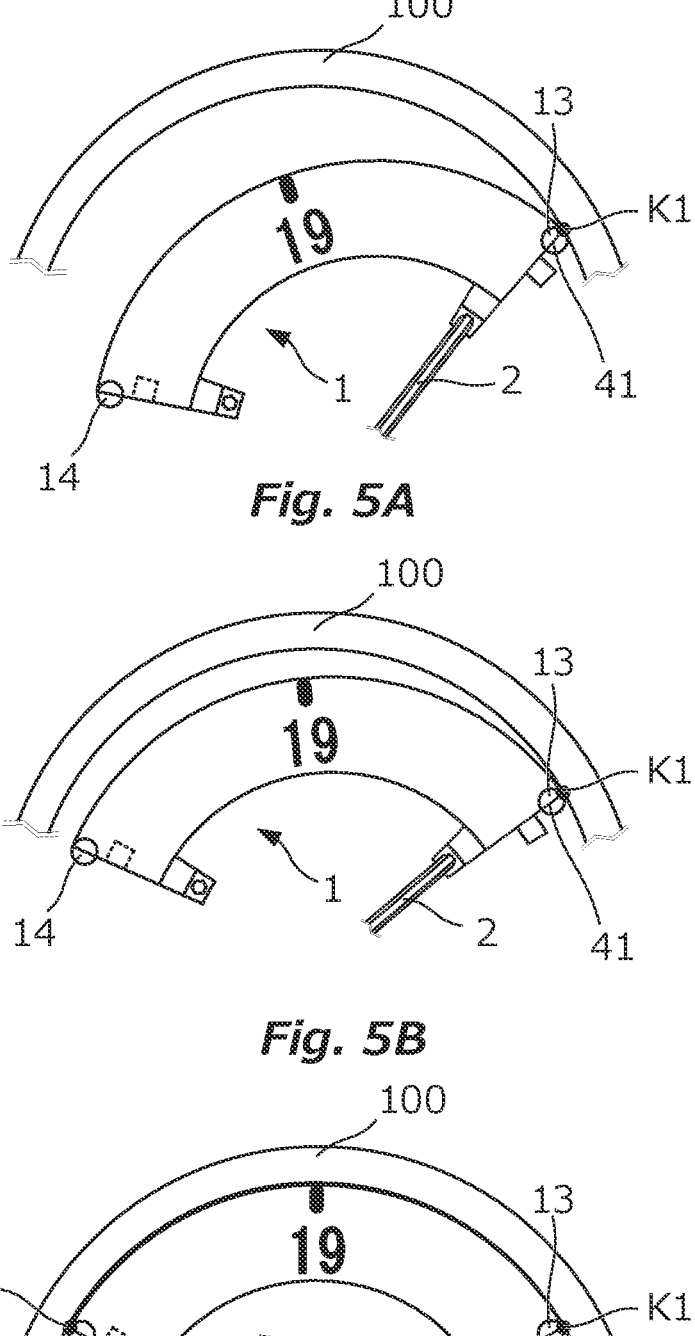
FIGS. 5A to 5C are a diagram describing a method of using the valve cusp sizer 1.

FIG. 5 is a diagram describing a method of using the valve cusp sizer 1. In the case of an aortic valvuloplasty, the valve cusp is cut from the aortic valve, and then the valve cusp sizer 1 supported by the support rod 2 is inserted into the aorta 100. Subsequently, in the case that the support rod 2 is inserted into the hole 22, the operator brings the first stylus part 13 into contact with the commissure part K1 that was located on the right side of the valve cusp before cutting the valve cusp as illustrated in FIG. 5A and then aligns the mark 41 in the first stylus part 13 with the commissure part K1. The operator brings the outer peripheral surface 10 into contact with the aorta 100 with the first stylus part 13 as a base point while rotating the support rod 2 as illustrated in FIG. 5B, and brings the second stylus part 14 into contact with the aorta 100 as illustrated in FIG. 5C.

The operator confirms the position where the second stylus part 14 is in contact with the aorta 100. If the position where the mark 41 in the second stylus part 14 is in contact is the position of the commissure part K2 that was located on the left side of the cut valve cusp before cutting the valve cusp, the value printed on the valve cusp sizer 1 that was used is the size of the valve cusp. If the position where the second stylus part 14 is in contact deviates from the position of the commissure part K2, the operator uses another valve cusp sizer 1 of a different size to measure the size of the valve cusp. If the position of the mark 41 of the first stylus part 13 matches the commissure part K1 and the position of the mark 41 of the second stylus part 14 matches the commissure part K2, the operator draws a mark indicating the start position for suturing with a skin marker at the position of the mark 40.

In the case where the support rod 2 is inserted in the hole 24, the valve cusp sizer 1 is inserted into the aorta 100, and then the second stylus part 14 is brought into contact with the commissure part K2. The operator brings the outer peripheral surface 10 into contact with the aorta 100 with the second stylus part 14 as a base point while rotating the support rod 2 and brings the first stylus part 13 into contact with the aorta 100 to measure the size of the valve cusp.

The aortic valve may have a congenital bivalvular cusp. In the case of the bivalvular cusp, the operator cuts the valve cusp before measuring the size of the valve cusp with the valve cusp sizer 1. For example, in the aortic valve having a congenital bivalvular cusp, there may be a raphe in a position different from the position of the two commissure parts. In this case, the operator considers the raphe as a commissure part and makes measurements in the same manner as in the case of three valve cusps. If there is no raphe in the congenital bivalvular cusp, there may be prepared a valve cusp sizer 1 with a large nominal diameter for size measurement of a valve cusp in the case of a bivalvular cusp. The operator calculates a value by adding the measured sizes and dividing the result by three. If the calculated value matches any of the nominal diameters of the valve cusp sizer 1, three valve cusp sizers 1 that match in the nominal diameter are connected in an annular shape. For example, if a value "21" is obtained by adding the measured sizes and dividing the result by three, the nominal diameter of the valve cusp sizer 1 is an odd number from 17 to 35, with a valve cusp sizer 1 corresponding to a value of 21; therefore three valve cusp sizers 1 each with a nominal diameter of 21 are prepared and connected to each other. As a valve cusp sizer for connecting to another valve cusp sizer, there is prepared a valve cusp sizer having a first stylus part 13 without a second stylus part 14 or a valve cusp sizer having a second stylus part 14 without a first stylus part 13. In providing a valve cusp sizer 1 with an even nominal diameter and if the value obtained by division by three is an even number, three valve cusp sizers 1 each having an even nominal diameter are prepared and connected to each other.

The operator arranges three valve cusp sizers 1 for annular connection in an annular shape and inserts the convex portion 31 of each valve cusp sizer 1 into the concave portion 32 of an adjacent valve cusp sizer 1 to connect the three valve cusp sizers 1 in an annular shape. The operator inserts the three valve cusp sizers 1 formed in the annular shape into the aorta and draws with a skin marker marks at the position where the first stylus part 13 is in contact with the inner wall of the aorta, the position where the second stylus part 14 is in contact therewith, and the position of the mark 40.

The calculated value may not match the nominal diameter of the valve cusp sizer 1. In this case, three valve cusp sizers 1 are selected so that the sum total of the nominal diameters of the three valve cusp sizers 1 to be connected matches the sum total of the measured sizes. For example, if the sum total of the measured sizes is 65, the value obtained by the division by three does not match an odd nominal diameter of the valve cusp sizer 1 from 17 to 35. In this case, three valve cusp sizers 1, for example, with nominal diameters of 23, 21, and 21 are connected so that the value matches the sum total of the measured values. In the case of providing valve cusp sizers 1 with even nominal diameters, valve cusp sizers 1 with even nominal diameters may be combined.

In the case where the hole into which the support rod 2 is inserted is in the center of the valve cusp sizer 1 in the left-right direction, the valve cusp sizer 1 is even in the left-right direction with respect to the support rod 2, and thus is stable. Therefore, when trying to bring the outer peripheral surface 10 into contact with the aorta 100, an action of pushing the valve cusp sizer 1 in the direction of the aorta 100 may be unwittingly performed. According to this embodiment, the hole into which the support rod 2 is inserted is located at the left and right ends of the valve cusp sizer 1, and the valve cusp sizer 1 is not even in the left-right direction with respect to the support rod 2. Therefore, an action is performed to rotate the valve cusp sizer 1 rather than to push the valve cusp sizer 1 in the direction of the aorta 100, and as a result of which the aorta 100 is less likely to be pushed radially by the valve cusp sizer 1, thereby inhibiting spread of the aorta 100, and enabling accurate measurement of the size of the valve cusp. Further, according to this embodiment, the portion to be supported 21 and the portion to be supported 23 are formed in the circumferential end portions in the circumferential view, and therefore it is easy to bring the first stylus part 13 or the second stylus part 14 into contact with the commissure part at start of the measurement. Further, according to this embodiment, the holes into which the support rods 2 are inserted are located at both ends in the circumferential direction, and therefore a right-handed operator and a left-handed operator are equally able to perform with ease measurement by changing the holes into which the support rods 2 are inserted. Moreover, according to this embodiment, in the case of performing an operation on a patient with two valve cusps to change the two valve cusps to three valve cusps, the three valve cusp sizers 1 are connected to form an annular shape, and the valve cusp sizers 1 connected in an annular shape are inserted into the aorta, thereby making it easier to mark the position of the commissure part and the start position for suturing the valve cusp, thereby facilitating the suture valve cusp.

Modifications

While the embodiments of the present invention have been described above, the present invention is not limited to the above-described embodiments, and may be implemented in various other ways. For example, the present invention may be carried out by modifying the above-described embodiments as described below. The above-described embodiments and the following modifications may be combined with each other.

The shape of the portion to be supported 21 and the shape of the portion to be supported 23 are not particularly limited, but preferably is basically a chamfered rectangular parallelepiped shape. Although not illustrated, the portion to be supported 21 and the portion to be supported 23 may have shapes that are different from those illustrated in the diagrams.

In the above-described embodiments, the hole 22 and the hole 24 are hexagonal holes, but the shapes of the hole 22 and the hole 24 may be polygons other than hexagons. Further, the shapes of the hole 22 and the hole 24 are not limited to polygons, and may be circular or elliptical. Further, while the hole 22 and the hole 24 are configured to be inclined with respect to the bottom surface 16 in the above-described embodiments, they may be configured not as not to be inclined.

In the present invention, when the support rod 2, the hole 22, and the hole 24 are screwed and the support rod 2 is inserted into the hole 22 or the hole 24, the support rod 2 may be fixed with a screw to the portion to be supported 21 or to the portion to be supported 23.

Although the valve cusp sizer 1 includes the portion to be supported 21 and the portion to be supported 23 in the above embodiments, the valve cusp sizer 1 may be configured to include only one of either the portion to be supported 21 or the portion to be supported 23.

Figure 6:
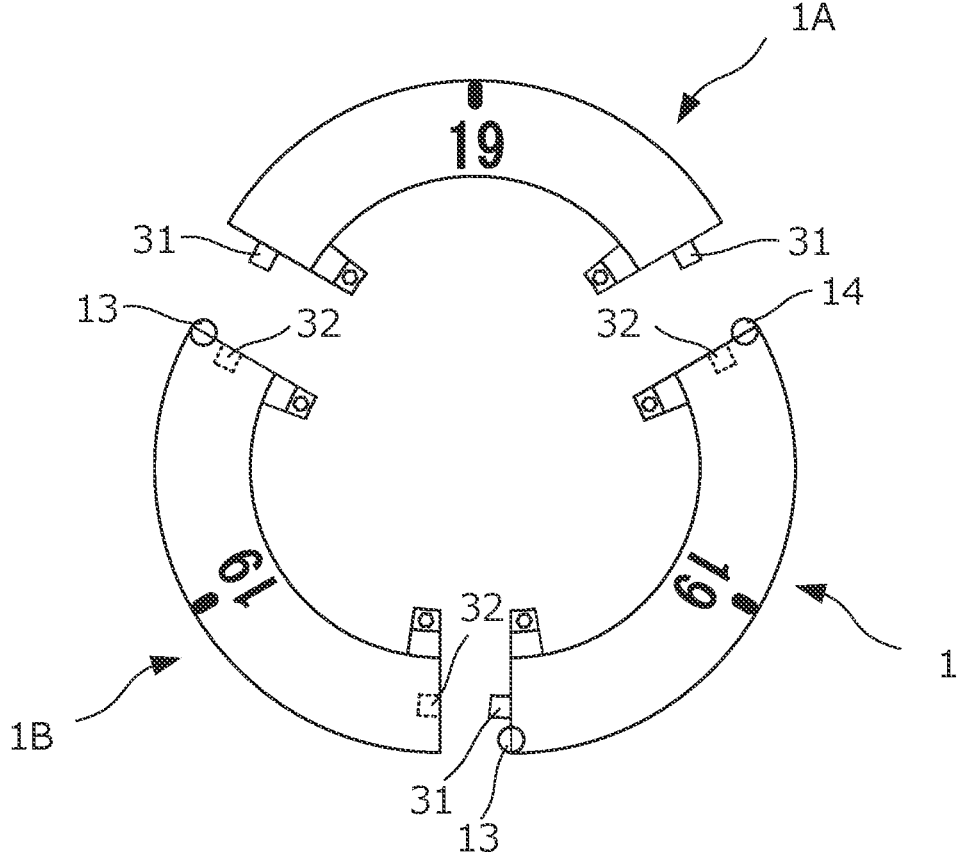
FIG. 6 is a diagram illustrating a valve cusp sizer 1A and a valve cusp sizer 1B according to a modification.

Although the valve cusp sizer 1 is configured to include the convex portion 31 and the convex portion 32 in the above embodiments, the valve cusp sizer 1 is not limited to the configuration that includes both. For example, a valve cusp sizer for use in a combination in an annular shape may be configured not to have the first stylus part 13 and the second stylus part 14, but to have convex portions 31 at both ends in the circumferential direction, as does the valve cusp sizer 1A illustrated in FIG. 6. Further, similar to the valve cusp sizer 1B illustrated in FIG. 6, the valve cusp sizer may be configured so as not to include the second stylus part 14, but to include concave portions 32 at both ends in the circumferential direction. If the valve cusp sizer 1, the valve cusp sizer 1A, and the valve cusp sizer 1B are arranged as illustrated in FIG. 6, the convex portion 31 is fitted to the concave portion 32 of another adjacent valve cusp sizer, such that the valve cusp sizer 1, the valve cusp sizer 1A, and the valve cusp sizer 1B are able to be connected in an annular shape.

Figure 7:
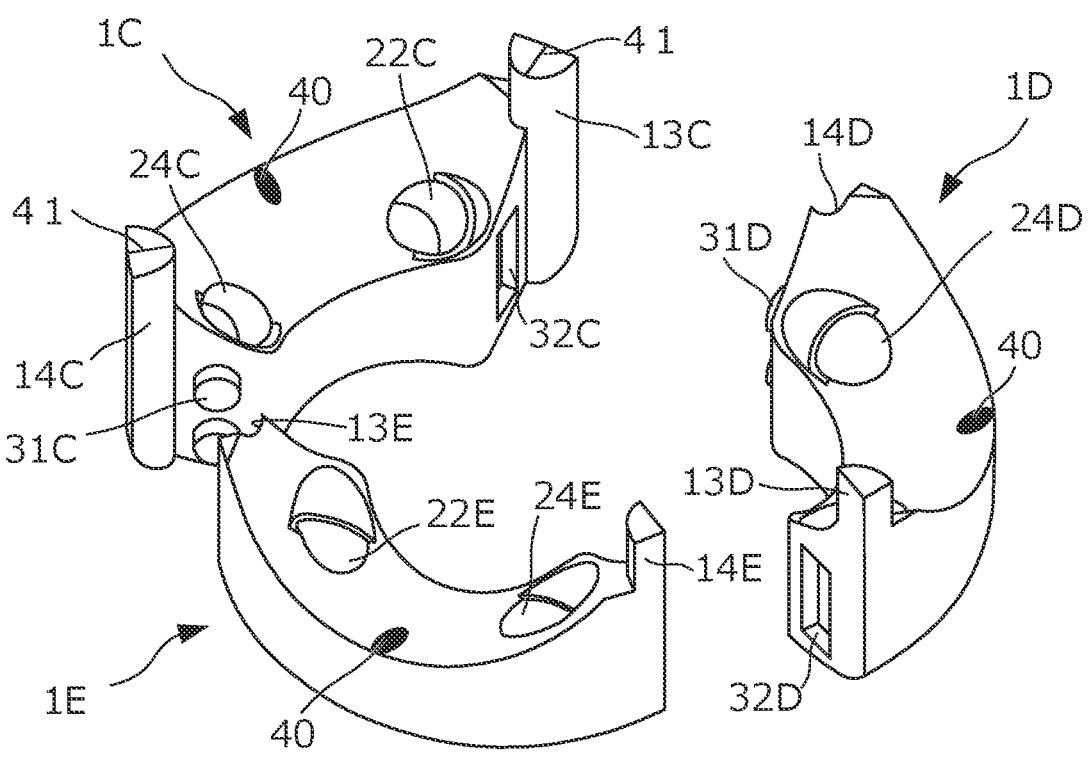
FIG. 7 is a diagram illustrating valve cusp sizers 1C to 1E according to a modification.

Although the valve cusp sizer 1 includes the portion to be supported 21 and the portion to be supported 23 in the above embodiments, the valve cusp sizer may be configured so as not to include the portion to be supported 21 and the portion to be supported 23. FIG. 7 is a diagram illustrating an example of a valve cusp sizer that does not include the portion to be supported 21 and the portion to be supported 23.

In a valve cusp sizer 1C, a semi-cylindrical first stylus part 13C is formed at one end in the circumferential direction, and a semi-cylindrical second stylus part 14C is formed at the other end in the circumferential direction. On the top surface of the valve cusp sizer 1C, a hole 22C into which the support rod is inserted is formed on one end side in the circumferential direction, and a hole 24C into which the support rod is inserted is formed on the other end side in the circumferential direction. The hole 22C is formed at a predetermined distance from the center in the left-right direction toward the right, and the hole 24C is formed at a predetermined distance from the center in the left-right direction toward the left. In the valve cusp sizer 1C, a concave portion 32C is formed on the end face on the side where the first stylus part 13C is located. In the valve cusp sizer 1C, a convex portion 31C is formed on the end face on the side where the second stylus part 14C is located.

In the valve cusp sizer 1D, a stylus part 13D having a fan-shaped cross section is formed at one end in the circumferential direction, and a concave portion 14D in which the first stylus part 13C fits is formed at the other end in the circumferential direction. On the top surface of the valve cusp sizer 1D, a hole 22D into which the support rod is inserted is formed on one end side in the circumferential direction, and a hole 24D (not illustrated) into which the support rod is inserted is formed on the other end side in the circumferential direction. The hole 22D is formed at a predetermined distance from the center in the left-right direction toward the right, and the hole 24D is formed at a predetermined distance from the center in the left-right direction toward the left. In the valve cusp sizer 1D, a concave portion 32D is formed on the end face on the side where the stylus part 13D is located. In the valve cusp sizer 1D, a convex portion 31D is formed on the end face on the side where the concave portion 14D is located.

In the valve cusp sizer 1E, a stylus part 14E having a fan-shaped cross section is formed at one end in the circumferential direction, and a concave portion 13E in which the second stylus part 14C fits is formed at the other end in the circumferential direction. On the top surface of the valve cusp sizer 1E, a hole 22E into which the support rod is inserted is formed on one end side in the circumferential direction, and a hole 24E into which a support rod is inserted is formed on the other end side in the circumferential direction. The hole 22E is formed at a predetermined distance from the center in the left-right direction toward the right, and the hole 24E is formed at a predetermined distance from the center in the left-right direction toward the left. In the valve cusp sizer 1E, a convex portion 31E (not illustrated) is formed on the end face on the side where the stylus part 14E is located. In the valve cusp sizer 1D, a concave portion 32E (not illustrated) is formed on the end face on the side where the concave portion 13E is located.

Figure 8:
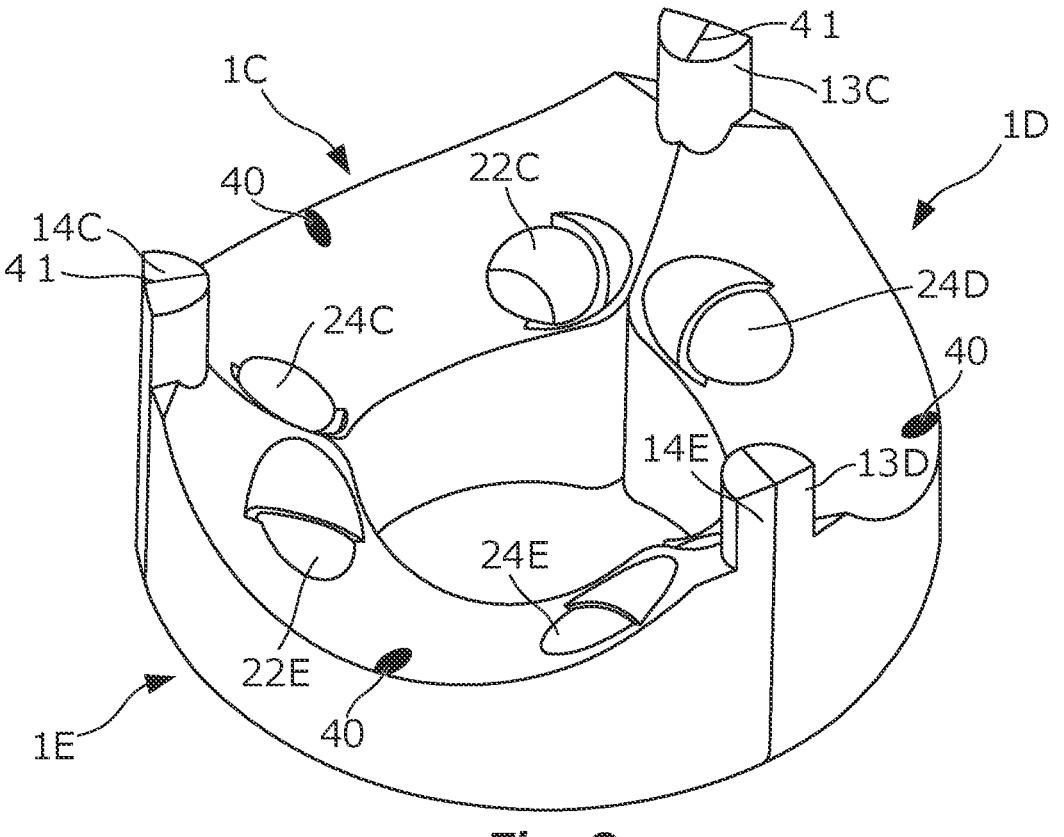
FIG. 8 is a diagram illustrating a state in which the valve cusp sizers 1C to 1E are connected to each other.

FIG. 8 is a diagram illustrating a state in which the valve cusp sizers 1C to 1D are connected to each other. When connecting the valve cusp sizers 1C to 1D, the convex portion provided on the end face in the circumferential direction fits in the concave portion provided in the circumferential direction of the adjacent valve cusp sizer. In addition, the first stylus part 13C fits in the concave portion 14D, the second stylus part 14C fits in the concave portion 13E, and the stylus part 13D and the stylus part 14E fit together, thereby enabling the valve cusp sizers 1C to 1E to be connected in an annular shape.

The valve cusp sizer 1D illustrated in FIG. 7 may be configured so that the shape of the stylus part 13D is the same as that of the first stylus part 13C, and the valve cusp sizer 1E may be configured so that a concave portion having the same shape as the concave portion 13E is provided at the position of the stylus part 14E.

In the above-described embodiments, the support rod 2 is inserted into the hole 22 or the hole 24. In the case, however, where the valve cusp sizer 1 is not connected to another valve cusp sizer 1 and is used only for measuring the size of the valve cusp, the support rod 2 may be integrated with the valve cusp sizer 1.

Figure 9:
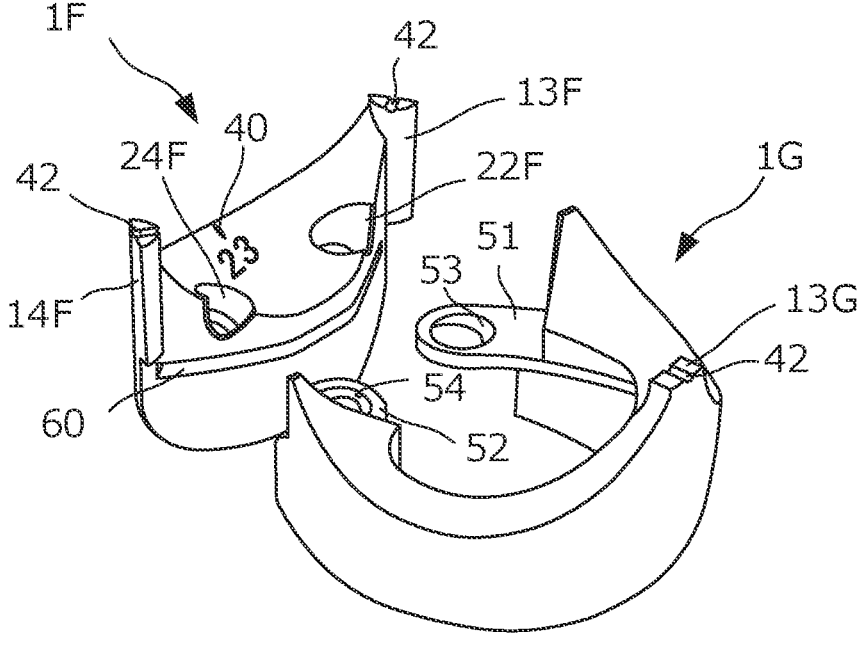
FIG. 9 is a diagram illustrating a valve cusp sizer 1F and a valve cusp sizer 1G according to a modification.

Although three valve cusp sizers are combined to form an annular shape in the above modification, the configuration in which multiple valve cusp sizers are connected to form an annular shape is not limited to the above configuration. FIG. 9 is a diagram illustrating an example of a valve cusp sizer 1F and a valve cusp sizer 1G according to a modification.

The basic shape of the valve cusp sizer 1G is a hollow cylinder divided into three equal parts relative to the central axis. In the valve cusp sizer 1F, a semi-cylindrical first stylus part 13F is formed at one end in the circumferential direction, and a semi-cylindrical second stylus part 14F is formed at the other end in the circumferential direction. At the upper end of the first stylus part 13F and the upper end of the second stylus part 14F, a groove 42 is formed as a mark for aligning the position of the commissure part. On the top surface of the valve cusp sizer 1F, a hole 22F into which a support rod is inserted is formed on one end side in the circumferential direction, and a hole 24F in which a support rod is inserted is formed on the other end side in the circumferential direction. The hole 22F is formed at a predetermined distance from the center in the left-right direction toward the right, and the hole 24F is formed at a predetermined distance from the center in the left-right direction toward the left. On the front of the valve cusp sizer 1F, a concave portion 60 is formed in a groove toward the back side. The opening of the concave portion 60 extends horizontally from the vicinity of the first stylus part 13F to the vicinity of the second stylus part 14F.

The valve cusp sizer 1G has a basic shape in which a hollow cylinder is divided into three equal parts relative to the central axis and one-third of the three equal parts is excluded. The valve cusp sizer 1G has a stylus part 13G in the center in the circumferential direction. On the top surface of the stylus part 13G, a groove 42, which is a mark for aligning the position of the commissure part, is formed. The arm part 51 has a plate-like shape protruding from one end of the valve cusp sizer 1G in the circumferential direction, and a hole 53 penetrating from the top surface to the bottom surface is formed at the tip. The arm part 52 has a plate-like shape protruding from the other end of the valve cusp sizer 1G in the circumferential direction, and a hole 54 penetrating from the top surface to the bottom surface is formed at the tip.

The arm part 51 and the arm part 52 are inserted into the concave portion 60 and the support rod is passed from the hole 22F to the hole 53 or from the hole 24F to the hole 54, by which the valve cusp sizer 1F and the valve cusp sizer 1G are brought into contact with each other to form an annular shape. For use of the bivalvular cusp in a patient, the valve cusp sizer 1F and the valve cusp sizer 1G, which are in contact with each other and form an annular shape, are inserted into an aorta, and one of the three grooves 42 is brought into contact with either one of the two commissure parts, and with a skin marker a mark is drawn at the positions of the remaining two grooves 42. In the valve cusp sizer 1F and the valve cusp sizer 1G, the valve cusp sizer 1F and the valve cusp sizer 1G may be integrated with each other in an annular shape by providing a concave portion and a convex portion on the end face in the circumferential direction and inserting the convex portion into the concave portion, as described in the embodiment. Further, in the case of providing a concave portion and a convex portion on the end face in the circumferential direction, as also described in the embodiment, in the valve cusp sizer 1F and the valve cusp sizer 1G, the arm part 51 and the arm part 52 may be omitted.

DESCRIPTION OF REFERENCE NUMERALS

1, 1A to 1G valve cusp sizers
2 support rod
10 outer peripheral surface
11 top surface
13, 13A to 13C first stylus parts
13D stylus part
14, 14C second stylus part
14D concave portion
14E stylus part
15 inner peripheral surface
16 bottom surface
17, 18 end face
21 portion to be supported
22, 22C to 22E holes
23 portion to be supported
24, 24C to 24E holes
31, 31C to 31E convex portions
32, 32C to 32E concave portions
40 to 41 marks
42 groove
51, 52 arm parts
53, 54 holes
100 aorta
K1, K2 commissure parts

The invention claimed is:

1. A valve cusp sizer comprising:
an outer peripheral surface having an arcuate shape and configured to be brought into contact with a living body;
a plurality of portions to be supported comprising a first portion to be supported and a second portion to be supported, each of the first portion to be supported and the second portion to be supported protruding from an inner peripheral surface of the valve cusp sizer, and the first portion to be supported being disposed at a first end in a circumferential direction of the valve cusp sizer and the second portion to be supported being disposed at a second end in the circumferential direction of the valve cusp sizer; and
each of the plurality of portions to be supported comprising a hole configured to receive a support rod, wherein each of the first portion to be supported and the second portion to be supported are positioned at a same distance from a center of the arcuate shape in a left-right direction.

2. The valve cusp sizer according to claim 1,
wherein a top surface of the valve cusp sizer comprises a top surface of each of the plurality of portions to be supported, and
wherein the hole of each of the plurality of portions to be supported is formed on the top surface of the valve cusp sizer.

3. The valve cusp sizer according to claim 2, wherein each hole is formed in the top surface of a corresponding one of the plurality of portions to be supported at a distal end from the inner peripheral surface of the valve cusp sizer.

4. The valve cusp sizer according to claim 2, wherein each hole is inclined relative to a bottom surface of the valve cusp sizer, the bottom surface being a surface opposite to the top surface of the top surface of the valve cusp sizer.

5. The valve cusp sizer according to claim 1, wherein each hole is formed in a corresponding one of the plurality of portions to be supported at a distal end thereof from the inner peripheral surface of the valve cusp sizer.

6. The valve cusp sizer according to claim 1, wherein each hole is inclined relative to a bottom surface of the valve cusp sizer.

7. The valve cusp sizer of claim 1, wherein each of the plurality of portions to be supported protrude orthogonally from the inner peripheral surface of the valve cusp sizer.

8. The valve cusp sizer of claim 1, wherein the outer peripheral surface of the valve cusp sizer defines an arc, and each of the plurality of portions to be supported protrude from the inner peripheral surface toward a center of the arc, the center of the arc being a center of an imaginary circle formed by the arc.

9. The valve cusp sizer according to claim 8, wherein
the outer peripheral surface and the inner peripheral surface have a substantially constant radial width with respect to the center of the arc along the circumferential direction of the valve cusp sizer from the left-side end and the right-side end.

10. The valve cusp sizer of claim 1, wherein the first end of the valve cusp sizer is a left-side end and the second end of the valve cusp sizer is a right-side end.

11. The valve cusp sizer of claim 1, wherein a shape of the hole corresponds to a shape of the support rod.

12. The valve cusp sizer of claim 1, wherein the hole has a hexagonal shape and the support rod has a hexagonal cross section.

13. The valve cusp sizer of claim 1, further comprising:
a convex portion protruding in the circumferential direction from a first end face of the valve cusp sizer; and
a concave portion extending in the circumferential direction into a second end face of the valve cusp sizer.

14. The valve cusp sizer of claim 13, wherein the convex portion and the concave portion are configured to be connecting means to other valve cusp sizers.

15. A valve cusp sizer comprising:
an outer peripheral surface having an arcuate shape and configured to be brought into contact with a living body;
a first portion to be supported protruding orthogonally from an inner peripheral surface of the valve cusp sizer at a left-side end in a circumferential direction of the valve cusp sizer;
a second portion to be supported protruding orthogonally from the inner peripheral surface of the valve cusp sizer at a right-side end in a circumferential direction of the valve cusp sizer,
wherein each of the first portion to be supported and the second portion to be supported comprise a hole configured to receive a support rod, and wherein each of the first portion to be supported and the second portion to be supported are positioned at a same distance from a center of the arcuate shape in a left-right direction.

16. The valve cusp sizer according to claim 15,
wherein a top surface of the valve cusp sizer comprises a top surface of each of the first portion to be supported and the second portion to be supported,
wherein the hole of each of the first portion to be supported and the second portion to be supported is formed on the top surface of the valve cusp sizer at a distal end thereof from the inner peripheral surface of the valve cusp sizer.

17. The valve cusp sizer according to claim 15, wherein each hole is inclined relative to a bottom surface of the valve cusp sizer, the bottom surface being a surface opposite to the top surface of the top surface of the valve cusp sizer.

18. The valve cusp sizer according to claim 16, wherein the outer peripheral surface of the valve cusp sizer defines an arc, and each of the first portion to be support and the second portion to be supported protrude from the inner peripheral surface toward a center of the arc, the center of the arc being a center of an imaginary circle formed by the arc.

19. The valve cusp sizer according to claim 18, wherein
the outer peripheral surface and the inner peripheral surface have a substantially constant radial width with respect to the center of the arc along the circumferential direction of the valve cusp sizer from the left-side end and the right-side end.

20. A plurality of valve cusp sizer, each valve cusp sizer of the plurality of valve cusp sizer comprising:
an outer peripheral surface having an arcuate shape and configured to be brought into contact with a living body;
a first portion to be supported protruding orthogonally from an inner peripheral surface of the valve cusp sizer at a left-side end in a circumferential direction of the valve cusp sizer;
a second portion to be supported protruding orthogonally from the inner peripheral surface of the valve cusp sizer at a right-side end in a circumferential direction of the valve cusp sizer;
a convex portion protruding in the circumferential direction from a first end face of the valve cusp sizer; and
a concave portion extending in the circumferential direction into a second end face of the valve cusp sizer,
wherein each of the first portion to be supported and the second portion to be supported comprise a hole configured to receive a support rod, and
wherein the convex portion is configured to be connected to the convex portion of other of the plurality of valve cusp sizers.

* * * * *